(12) United States Patent
Kellogg et al.

(10) Patent No.: US 7,963,917 B2
(45) Date of Patent: Jun. 21, 2011

(54) SYSTEM AND METHOD FOR CONTINUOUS NON-INVASIVE GLUCOSE MONITORING

(75) Inventors: Scott Kellogg, Boston, MA (US); Han Chuang, Canton, MA (US); Shikha Barman, Bedford, MA (US); Nick Warner, Belmont, MA (US)

(73) Assignee: Echo Therapeutics, Inc., Franklin, MA (US)

( * ) Notice: Subject to any disclaimer, the term of this patent is extended or adjusted under 35 U.S.C. 154(b) by 1432 days.

(21) Appl. No.: 11/275,038

(22) Filed: Dec. 5, 2005

(65) Prior Publication Data

US 2007/0129621 A1    Jun. 7, 2007

(51) Int. Cl.
*A61B 5/00* (2006.01)
*A61B 5/05* (2006.01)

(52) U.S. Cl. ....................... 600/365; 600/347
(58) Field of Classification Search .......... 600/300, 600/309, 345–366
See application file for complete search history.

(56) References Cited

U.S. PATENT DOCUMENTS

| | | | |
|---|---|---|---|
| 5,497,772 A * | 3/1996 | Schulman et al. | 600/347 |
| 5,660,163 A * | 8/1997 | Schulman et al. | 600/345 |
| 5,722,397 A * | 3/1998 | Eppstein | 600/345 |
| 6,175,752 B1 * | 1/2001 | Say et al. | 600/345 |
| 6,180,416 B1 * | 1/2001 | Kurnik et al. | 600/316 |
| 6,272,364 B1 * | 8/2001 | Kurnik | 600/345 |
| 6,546,269 B1 * | 4/2003 | Kurnik | 600/345 |
| 6,553,244 B2 * | 4/2003 | Lesho et al. | 600/347 |
| 6,560,471 B1 * | 5/2003 | Heller et al. | 600/347 |
| 6,561,978 B1 * | 5/2003 | Conn et al. | 600/309 |
| 6,565,509 B1 * | 5/2003 | Plante et al. | 600/365 |
| 6,572,542 B1 * | 6/2003 | Houben et al. | 600/300 |
| 6,591,124 B2 * | 7/2003 | Sherman et al. | 600/345 |
| 6,633,772 B2 * | 10/2003 | Ford et al. | 600/345 |
| 6,692,456 B1 * | 2/2004 | Eppstein et al. | 604/22 |
| 6,809,653 B1 * | 10/2004 | Mann et al. | 340/870.28 |
| 6,862,466 B2 * | 3/2005 | Ackerman | 600/347 |
| 6,882,940 B2 * | 4/2005 | Potts et al. | 702/23 |
| 6,885,883 B2 * | 4/2005 | Parris et al. | 600/347 |
| 6,941,163 B2 * | 9/2005 | Ford et al. | 600/347 |
| 6,990,366 B2 * | 1/2006 | Say et al. | 600/345 |
| 7,003,341 B2 * | 2/2006 | Say et al. | 600/345 |
| 7,011,630 B2 * | 3/2006 | Desai et al. | 600/309 |
| 7,024,236 B2 * | 4/2006 | Ford et al. | 600/345 |
| 7,066,884 B2 * | 6/2006 | Custer et al. | 600/309 |

(Continued)

*Primary Examiner* — Charles A Marmor, II
*Assistant Examiner* — Navin Natnithithadha
(74) *Attorney, Agent, or Firm* — Hunton & Williams LLP

(57) ABSTRACT

A system and method for continuous non-invasive glucose monitoring is disclosed. According to one embodiment of the present invention, the method includes the steps of (1) contacting a remote device to an area of biological membrane having a permeability level, the remote device comprising a sensor and a transmitter; (2) extracting the at least one analyte through and out of the area of biological membrane and into the sensor; (3) generating an electrical signal representative of a level of the at least one analyte; (4) transmitting the electrical signal to a base device; (5) processing the electrical signal to determine the level of the at least one analyte; and (6) displaying the level of the at least one analyte in real time. The system includes a remote device that includes a sensor that generates an electrical signal representative of the concentration of the at least one analyte; and a transmitter that transmits the electrical signal. The system further includes a base device that includes a receiver that receives the electrical signal; a processor that processes the electrical signal; and a display that displays the processed signal in real time.

13 Claims, 12 Drawing Sheets

U.S. PATENT DOCUMENTS

| | | | |
|---|---|---|---|
| 7,098,803 B2 * | 8/2006 | Mann et al. | 340/870.07 |
| 7,150,975 B2 * | 12/2006 | Tamada et al. | 435/14 |
| 7,163,511 B2 * | 1/2007 | Conn et al. | 600/309 |
| 7,190,988 B2 * | 3/2007 | Say et al. | 600/345 |
| 7,228,163 B2 * | 6/2007 | Ackerman | 600/347 |
| 7,324,012 B2 * | 1/2008 | Mann et al. | 340/870.07 |
| 7,399,277 B2 * | 7/2008 | Saidara et al. | 600/300 |
| 7,602,310 B2 * | 10/2009 | Mann et al. | 340/870.07 |
| 7,604,593 B2 * | 10/2009 | Parris et al. | 600/365 |
| 7,699,775 B2 * | 4/2010 | Desai et al. | 600/365 |

* cited by examiner

SYSTEM AND METHOD FOR CONTINUOUS NON-INVASIVE GLUCOSE MONITORING

BACKGROUND OF THE INVENTION

1. Field of the Invention

The present invention generally relates to transdermal transport using ultrasound or other skin permeation methods, and, more particularly, to a system and method for continuous non-invasive glucose monitoring.

2. Description of Related Art

The benefits of an intensive glucose management protocol on the mortality of critically ill adult patients is starting to be understood. Dr. James Stephen Krinsley has reported that, in a study recently conducted at the Intensive Care Unit at Stamford Hospital, a protocol that attempts to keep blood glucose levels lower than 140 mg/dL was associated with a significant decrease in motality among critically ill patients. See Krinsley, James Stephen "Effect of Intensive Glucose Management Protocol on the Mortality of Critically Ill Adult Patients," *Mayo Clin Proc*. August 2004; 79(8): 992-1000 (the contents of which are incorporated by reference in their entirety).

Before Dr. Krinsley's protocol was introduced, the standard of care at the ICU, which was typical for most ICUs, was to tolerate moderate levels of hyperglycemia. Thus, insulin was typically not administered unless the blood glucose levels exceeded 200 mg/dL on two successive finger sticks. If the blood glucose level was not above 200 mg/dL, no treatment was provided.

With Krinsley's protocol in place, the glucose levels of patients in the ICU was initially to be measured at least every three hours. To accomplish this, nurses were required to perform a finger stick initially every three hours to obtain a glucose value. If the glucose value exceeded 200 mg/dL on two successive finger sticks, intravenous insulin was administered to the patient. For lower glucose levels, subcutaneous regular insulin was administered. If the glucose value was below 140 mg/dL, no treatment was administered.

Dr. Krinsley's protocol imposed a significant amount of extra work on the nursing staff at the hospital. It required a willingness and commitment on behalf of the nursing staff to take repeated glucose measurements, and by a finger stick.

SUMMARY OF THE INVENTION

According to one embodiment of the present invention, a method for real time remote monitoring and display of a level of at least one analyte in a body fluid of a subject is disclosed. The method includes the steps of (1) contacting a remote device to an area of biological membrane having a permeability level, the remote device comprising a sensor and a transmitter; (2) extracting the at least one analyte through and out of the area of biological membrane and into the sensor; (3) generating an electrical signal representative of a level of the at least one analyte; (4) transmitting the electrical signal to a base device; (5) processing the electrical signal to determine the level of the at least one analyte, and (6) displaying the level of the at least one analyte in real time.

According to another embodiment of the present invention, a system for real time remote monitoring of a level of at least one analyte in a body fluid is disclosed. The system includes a remote device that includes a sensor that generates an electrical signal representative of the concentration of the at least one analyte; and a transmitter that transmits the electrical signal. The system further includes a base device that includes a receiver that receives the electrical signal; a processor that processes the electrical signal; and a display that displays the processed signal in real time.

According to another embodiment of the present invention, a transdermal sensor is disclosed. The transdermal sensor includes a substrate having a first and a second surface. A first electrode trace is formed on the first surface of the substrate. A second electrode trace is formed on the second surface of the substrate. A third electrode trace is formed on the second surface of the substrate. A fourth electrode trace is formed on the second surface of the substrate. A fifth electrode trace is formed on the second surface of the substrate. A dielectric is formed on the second surface of the substrate. A plurality of electrical contacts are provided.

It is a technical advantage of the present invention that a system for continuous non-invasive glucose monitoring is disclosed. It is another technical advantage of the present invention that a method for continuous non-invasive glucose monitoring is disclosed. It is another technical advantage of the present invention that a transdermal sensor is disclosed. It is still another technical advantage of the present invention that a remote device and a base device are disclosed. It is another technical advantage of the present invention that the remote device and the base device may communicate by a wireless protocol, such as a wireless application protocol link, a general packet radio service link, a Bluetooth radio link, an IEEE 802.11-based radio frequency link, a RS-232 serial connection, an IEEE-1394 (Firewire) connection, a fibre channel connection, an infrared (IrDA) port, a small Computer Systems Interface (SCSI) connection, and a Universal Serial Bus (USB) connection.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF PREFERRED EMBODIMENTS

Figure 1:
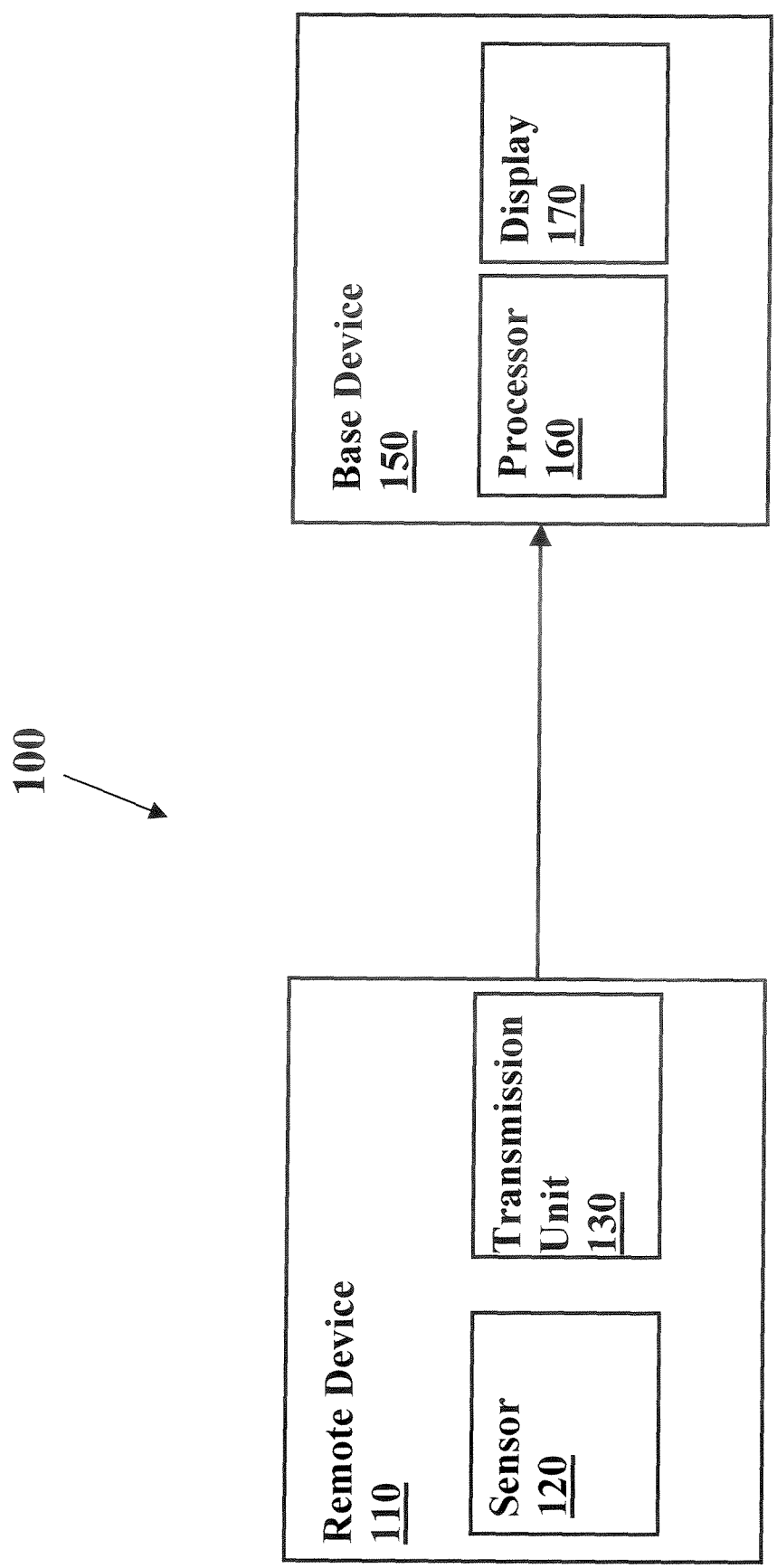
FIG. 1 illustrates a block diagram of a system for continuous, noninvasive monitoring of a subject's glucose levels according to one embodiment of the invention.

Preferred embodiments of the present invention and their advantages may be understood by referring to FIGS. 1-12, wherein like reference numerals refer to like elements, and are described in the context of a portable skin permeation system for pretreating an area of skin with ultrasound and then transdermally extracting a continuous flux of glucose to be measured by a sensor.

It is known that ultrasound can be used to increase the permeability of the skin, thereby allowing the extraction of analytes, such as glucose, through the skin. For example, U.S. Pat. No. 6,234,990 to Rowe et al., the disclosure of which is hereby incorporated by reference, discloses methods and devices using a chamber and ultrasound probe to non-invasively extract analyte and deliver drugs (i.e., broadly transdermally transport substances). This provides many advantages, including the ability to create a small puncture or localized erosion of the skin tissue, without a large degree of concomitant pain. The number of pain receptors within the ultrasound application site decreases as the application area decreases. Thus, the application of ultrasound to a very small area will produce less sensation and allow ultrasound and/or its local effects to be administered at higher intensities with little pain or discomfort.

By applying a brief duration of ultrasound, the outer most layer of skin (i.e., stratum corneum) becomes permeable. In an exemplary embodiment of the invention, the area of the pretreated skin site is approximately 0.8 $cm^2$. In-vivo studies demonstrate that skin conductivity is significantly enhanced by ultrasound pretreatment and that the enhancement lasts for approximately twenty-four (24) hours. In order to control the ultrasound pretreatment, particularly the duration thereof, the change in skin conductance (or impedance) is measured during the application of ultrasound. When a desired level of skin conductivity is achieved, and hence a desired level of skin permeability, application of ultrasound is terminated. After permeation, passive diffusion or iontophoresis enhances the transport of a drug, such as an anesthetic agent across the treated skin site. In the case of ion ophoresis, a low-level current to a drug delivery electrode and a grounding electrode are employed. The potential difference between the two electrodes allows the drug ions to migrate efficiently from the drug delivery electrode into the skin. The delivery dose is proportional to the level of applied current and the treatment time. Similarly, analytes can be passively or iontophoretically transported across the skin for measurement.

Moreover, U.S. Pat. No. 6,190,315 to Kost et al., the disclosure of which is incorporate by reference, discloses that application of ultrasound is only required once for multiple deliveries or extractions over an extended period of time rather than prior to each extraction or delivery. That is, it has been shown that if ultrasound having a particular frequency and a particular intensity of is applied, multiple analyte extractions or drug deliveries may be performed over an extended period of time. For example, if ultrasound having a frequency of 20 kHz and an intensity of 10 $W/cm^2$ is applied, the skin retains an increased permeability for a period of up to four hours.

Nevertheless, the amount (e.g., duration, intensity, duty cycle) of ultrasound necessary to achieve this permeability enhancement varies widely. Several factors on the nature of skin must be considered. For example, the type of skin which the substance is to pass through varies from species to species, varies according to age, with the skin of an infant having a greater permeability than that of an older adult, varies according to local composition, thickness and density, varies as a function of injury or exposure to agents such as organic solvents or surfactants, and varies as a function of some diseases such as psoriasis or abrasion.

Once the permeability of the skin is increased, by ultrasound or by another means, the system of the present invention may be implemented. FIG. 1 illustrates a block diagram of a system for continuous, noninvasive monitoring of a subject's glucose levels according to one embodiment of the invention. System 100 generally includes remote device 110 and base device 150. Remote device 110, which preferably includes sensor 120, is provided to a subject and produces a signal (e.g., an amperometric current signal) related to an analyte concentration, such as glucose, in the subject. Remote device 110 may consist of a reusable assembly that produces a signal that represents the magnitude of the current produced by transdermal sensor. Remote device may also produce signals that represent the subject's skin temperature and the charge level of batteries. Remote device 110 also preferably includes transmission unit 130 that transmits the signal to base device 150. Remote device may also include a unique identifier, such as an identification number.

Base device 150 preferably includes processor 160 that processes the signal to determine the analyte concentration in the subject. Base device 150 preferably also includes display 170 that displays the results for a user.

Figure 2:
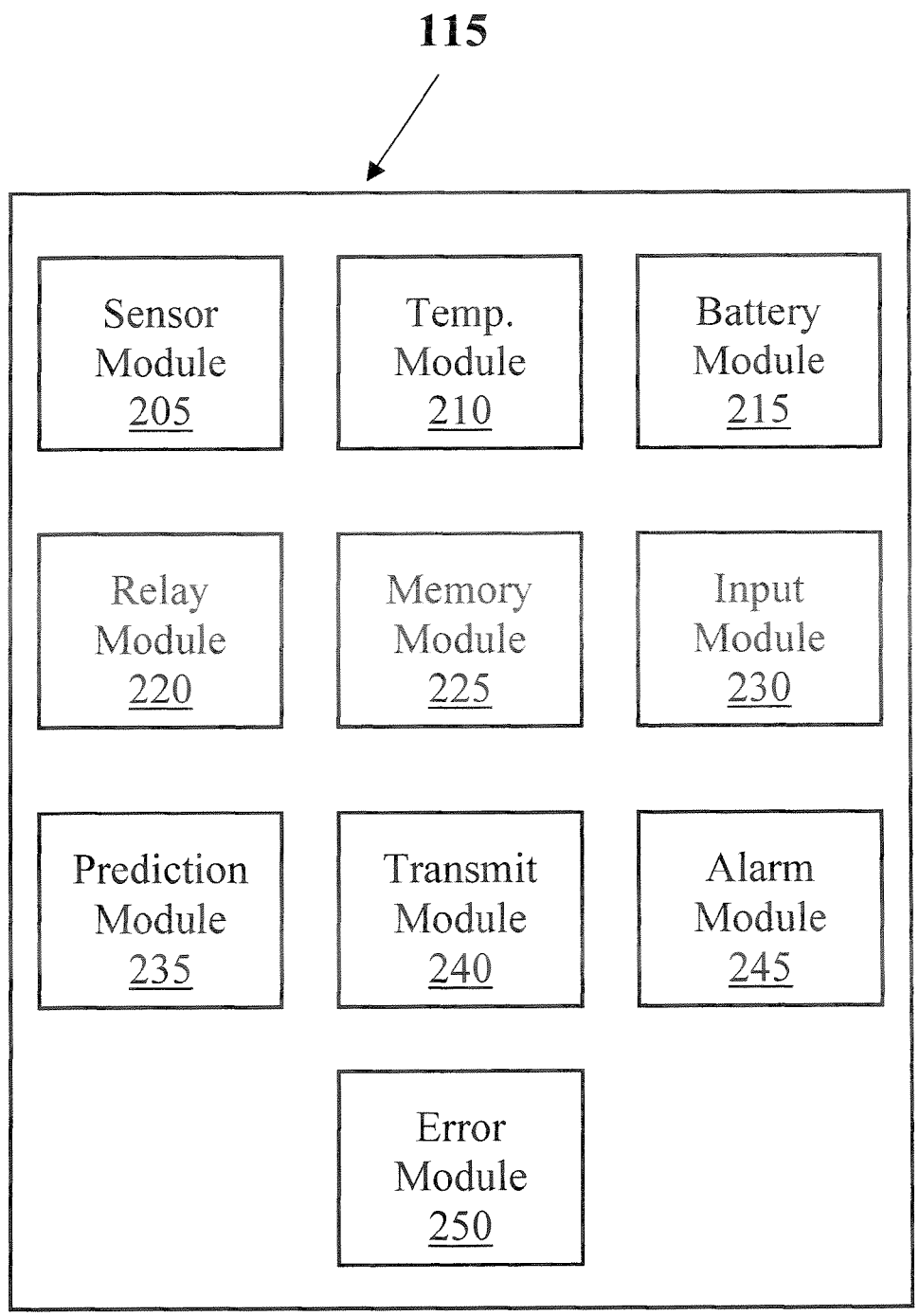
FIG. 2 illustrates exemplary modules that may be associated with system of FIG. 1.

FIG. 2 illustrates exemplary modules that may be associated with system 100 for carrying out the various functions and features of the embodiments described herein. In some embodiments, the modules may be included that perform the following functions: (1) quantify the current produced by remote device 110; (2) measure the subject's skin temperature; (3) measure the voltage level of a battery that may be used to power system 100; (4) transmit data among system 100 modules; (5) receive data representing measured values and store them in memory units; (6) receive at least a calibration standard for the subject's glucose level via an input device; (7) predict the subject's glucose level, the glucose level's rate of change, and the percent change in the user's skin temperature; (8) transmit data to base device 130; (9) operate the device's alarm functions; and (10) operate the device's error functions. A brief description of each module is provided below. Although the modules are discussed individually by function, it should be understood that a single module may perform more than one function, or, alternatively, that more than one module may be required to perform one function.

Sensor module 205 may monitor the amperometric current produced at remote device 110 and produce a time-stamped measurement of its magnitude. In some embodiments of the system 100, sensor module 205 may use a potentiostat to measure this current. This value is related to the subject's glucose level.

Temperature module 210 may produce a time-stamped measurement of the subject's skin temperature. In some embodiments of the system 100, temperature module 210 may use a thermally sensitive resistors (i.e., a thermistor) to measure the temperature. Other mechanisms for measuring the subject's skin temperature may also be used.

Battery module 215 may measure the voltage level of battery or other power source that may be used to power at least some of the modules in system 100. In some embodiments of system 100, battery module 215 may use a voltmeter to measure this value.

Relay module 220 may transmit data among at least some of the modules of system 100 using any wired or wireless, digital or analog interface or connection. In some embodiments of system 100, relay module 220 may use a radio frequency transmitter to transmit data among modules.

Memory module 225 may receive data sent from relay module 220 and store it in memory units. Any suitable type of memory may be used. In one embodiment, a non-volatile memory that can store seven days of data may be used. Other types and sizes of memory may be used as appropriate.

Input module 230 may allow a user to enter data for the system, such as glucose level calibration data. This may be based on a measurement taken from a blood sample. In some embodiments of system 100, input module 230 may use a keypad to allow a user to input calibration data.

Prediction module 235 may combine calibration data with the signals representing the current in remote device 110 to predict the subject's current glucose level, the glucose level's rate of change, and the percent change of the subject's skin temperature. In some embodiments of system 100, prediction module 235 may include a microcontroller to predict a subject's glucose levels.

Transmit module 240 may transmit a signal to base device 150 using any wired or wireless, digital or analog interface or connection. In some embodiments of the system, this signal may contain data representing, for example, the current in remote device 110, the subject's predicted glucose value, the predicted rate of change of the subject's glucose value, the measured current voltage of batteries, the percent change of the subject's skin temperature, etc.

Transmit module 240 may also transmit a signal to a hospitals central patient database.

Alarm module 245 may allow the user to set parameters for the devices' alarm function. These alarms may be set to become active when certain conditions are met, such as when the subject's glucose level reach certain values, when a predicted rate of change reaches a certain value, or when battery voltages reach a certain level. The alarms will be discussed in greater detail, below.

Error module 250 may verify that any data transmitted between system 150 modules is transmitted accurately and securely.

In some embodiments of the invention, modules associated with system 100 may be located independently, with remote device 110, with base device 150, or located with both. For example, in system 100, sensor module 205, temperature module 210, battery module 215, relay module 220, and transmit module 240 may be colocated with remote device 110. In this embodiment, the remaining modules of system 100 may be located with base device 150.

Figure 3A:
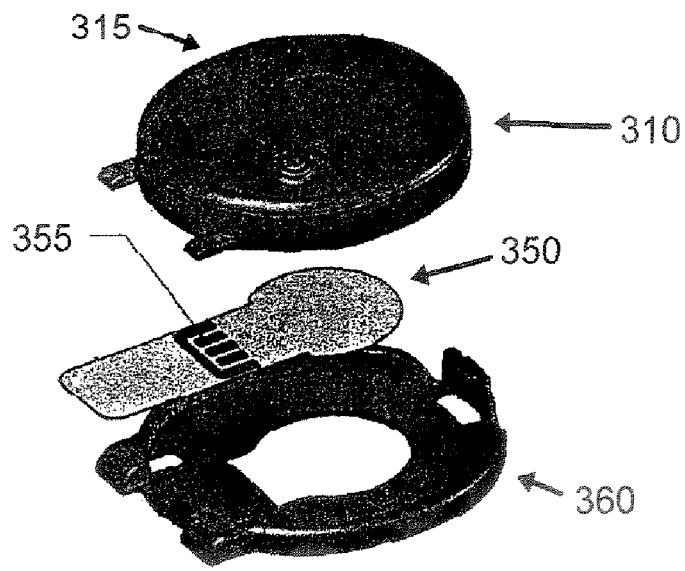
FIG. 3a is a top perspective view of and FIG. 3b is a bottom perspective view of a remote device according to one embodiment of the present invention.
Figure 3B:
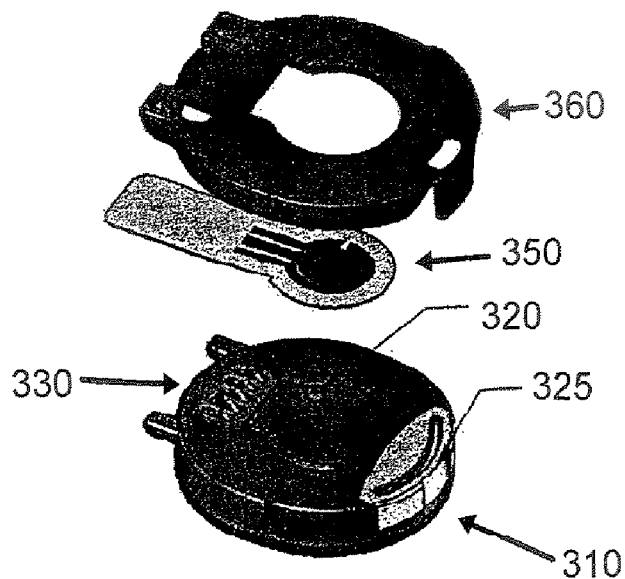

Referring to FIGS. 3a and 3b, an exemplary embodiment remote device 110 is provided. FIG. 3a is a top perspective view of remote device 110 and FIG. 3b is a bottom perspective view of remote device 110. Upper portion 310 of remote device 110 includes operational indicator 315, such as a LED, temperature module 320, such as a thermistor, battery 325, and contacts 330 for making contact with contacts 355 on sensor 350. Upper portion 310 may also include relay module (not shown) and transmit module (not shown).

Lower portion 360 of remote device 110 includes target ring 365 and adhesive 370.

The upper portion 310 and lower portion 360 of remote device 110 preferably interface so they are easily detachable after use, but are not easily detachable during use. In one embodiment, lower portion 360 is disposable, while upper portion 310 is reuseable.

Although remote device 110 and certain portions thereof are illustrated as being circular, other geometries may be used as necessary.

Figure 4:
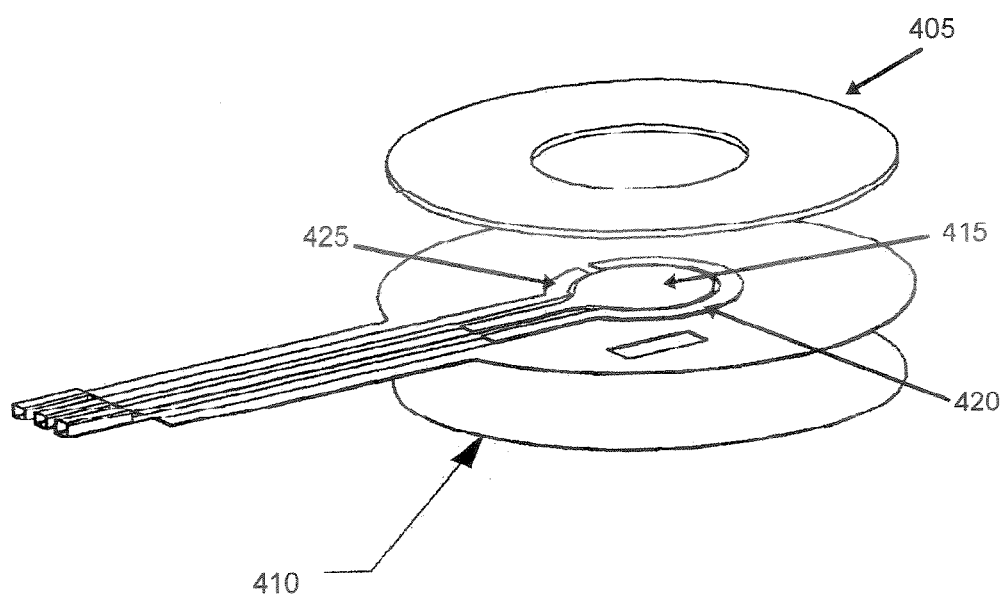
FIG. 4 is an illustration of a sensor according to one embodiment of the present invention.

Referring to FIG. 4, an illustration of sensor 350 according to one embodiment of the present invention is provided. Sensor 350 includes adhesives 405 and 410. Adhesives 405 and 410 may be commercially-available medical adhesives. In one embodiment, adhesive 405 may be an adhesive ring MED 3044 with a 9/16 inch inner diameter, and a 1 3/8 inch outer diameter, and adhesive 410 may be an adhesive disc MED 3044 with a 1 3/8 inch diameter. Both are available from Avery Dennison, 150 North Orange Grove Boulevard, Pasadena, Calif. 91103-3596, USA.

Sensor 350 also includes working electrode 415, counter electrode 420, and reference electrode 425. In one embodiment, working electrode 415 is formed by sputter coating pure platinum (Pt) material, and both counter electrode 420 and reference electrode 425 are formed by screen printing carbon and Ag/AgCl materials.

Figure 5:
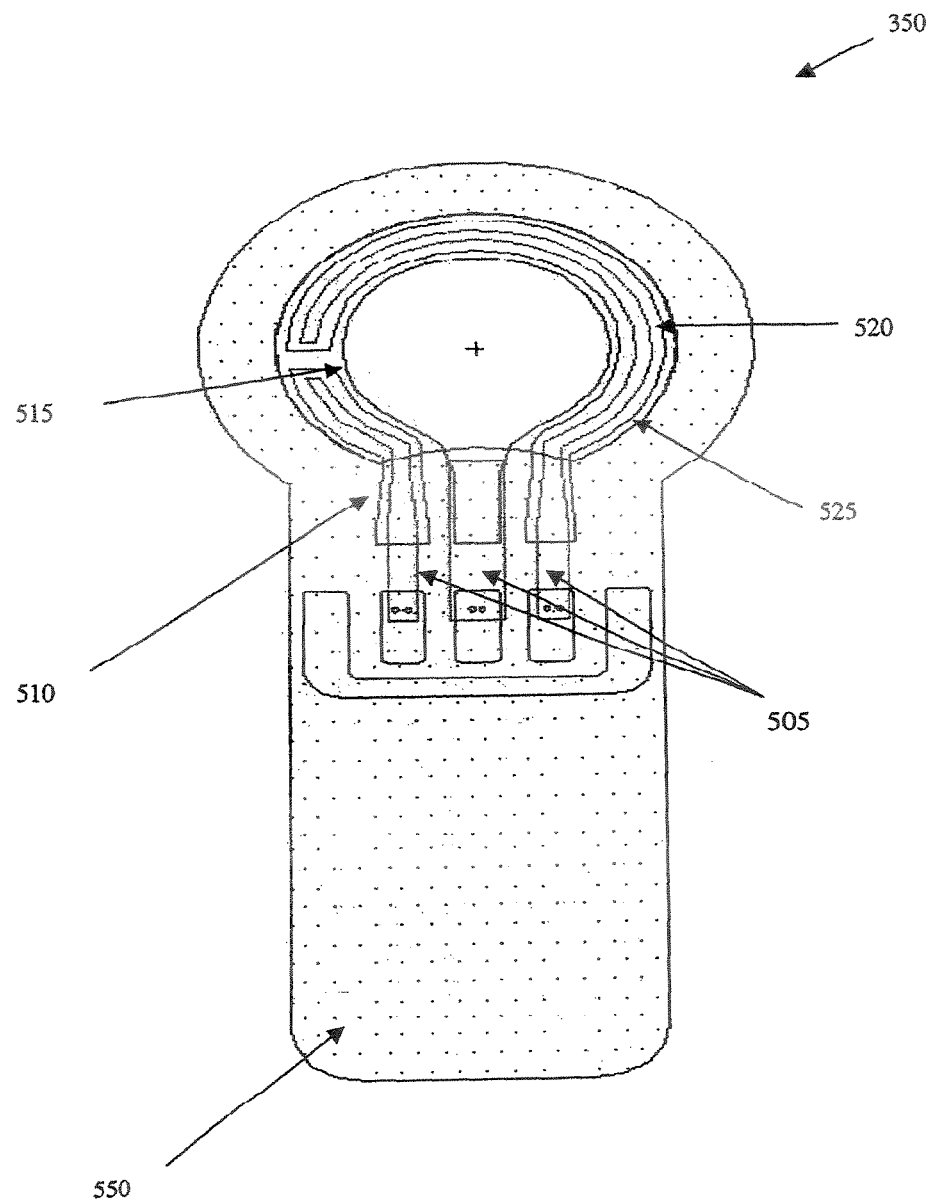
FIG. 5 is an illustration of a transdermal sensor according to one embodiment of the present invention.

Referring to FIG. 5, an illustration of sensor 350 according to one embodiment of the present invention is provided. Electrode 500 may of sensor 350 has an outer diameter of 9/16". Electrode 500 is mounted on substrate 550, which is preferably heat annihilated PET. Electrode 500 includes, on a front surface of substrate 550, silver 505 on a front of substrate 550, silver/silver chloride 510, platinum 515, carbon 520, and clear dielectric 525. On a back surface of substrate 550, silver (not shown) is provided. Connection points to electronics are located on the back of the sensor using a mill-and-fill and printing process by CTI.

Sensor 350 may be provided with a hyrdogel (not shown). In one embodiment, hydrogel may be polyethylene glycol diacrylate (PEG-DA) hydrogel with entrapped glucose oxidase (GOx). Such a hydrogel is disclosed in U.S. patent application Ser. No. 11/275,043, entitled "Biocompatible Chemically Crosslinked Hydrogels For Glucose Sensing," filed Dec. 2, 2005, the disclosure of which is incorporated reference in its entirety. The hydrogel may be sized to be inserted in the inner diameter of adhesive 405.

Once sensor 355 is connected and adhered to the subject's skin, it may begin to produce a signal representing an amperometric current proportionate to the subject's glucose level.

Figure 6:
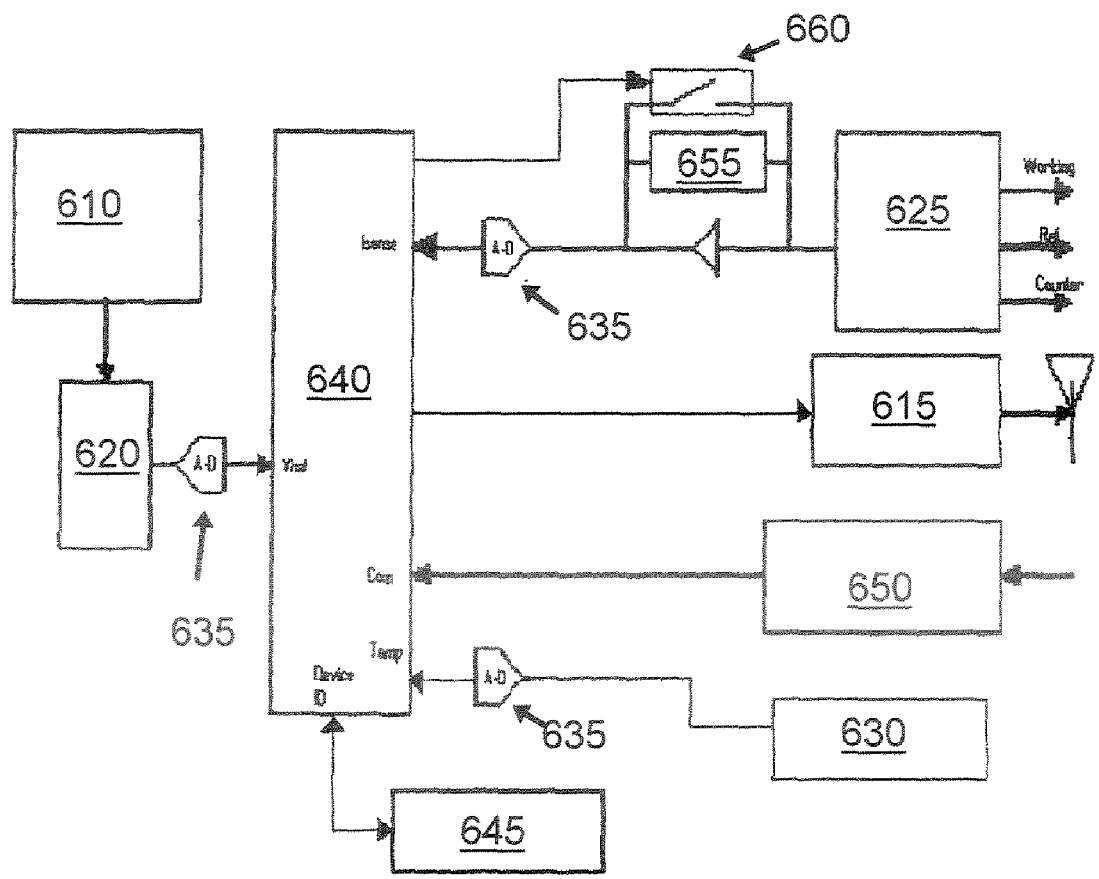
FIG. 6 is a detailed schematic for a remote device according to one embodiment of the present invention.

Referring to FIG. 6, a detailed schematic for remote device 110 according to one embodiment of the present invention is provided. Remote device 110 includes switch 610. Switch 610 may be a contact switch that is triggered when remote device 110 is secured to a subject. For example, transmitter 615 may be electrically disconnected until remote device 110 is secured to a subject.

Remote device 110 also includes battery 620. In one embodiment, battery 620 is a single 3V Lithium "coin-cell." It is anticipated that this type of battery will power remote device 110 for a minimum of 1 week. In one embodiment, the voltage of battery 620 is transmitted to and monitored by base device 150. This voltage may be transmitted at a predetermined time interval, discussed below.

Potentiostat 625 is provided to quantify the amperometric current produced by sensor 350. In one embodiment, potentiostat 625 sets remote device 110 at a predetermined voltage, such as 500 mV. Once set, sensor 350 will initially start with a high current, such as 50 μA and then ramps down to 200 nA. While at a high current, it is important that potentiostat 625 does not saturate (i.e., the working electrode moves above ground). For this reason, currents above 1 μA will be detected with a low value resistor (kOhms) and currents below 1 μA will be accurately measured with a high value resistor (MOhms).

In one embodiment, potentiostat 625 is bi-polar, splitting the supply voltage in half. For example, potentiostat 625 may split supply voltage 3 V DC into ±1.5 V DC. Because, in one embodiment, the data from potentiostat 625 is downloaded to base device 150 periodically, adequate filtering and roll-off may be provided to average the data over the predetermined time interval.

In addition, signal filtering (not shown) may be provided to reduce spurious noise events, such as current spikes on the order of 5 nA to 10 nA, or greater per minute.

Thermistor 630 is provided to monitor the temperature near the surface of the subject's skin. In one embodiment, this data may be transmitted to base device 150 at a predetermined interval, discussed below.

Analog to digital (A/D) converters 635 are provided to digitize the outputs of potentiostat 625, thermistor 630, and the voltage of battery 620. In one embodiment, this data is collected and stored in memory for transmission to base device 150. Although three A/D converters 635 are illustrated in FIG. 5, additional A/D converters may be used, or a single A/D converter with a multiplexed input may also be used.

Controller 640, which may be a miniature low power controller or state machine is provided to coordinate all hardware interaction. Controller 640 will be discussed in greater detail, below.

Memory 645 is provided to store a unique identifier that is common between the transmitter 615 and base device 150. In one embodiment, base device 150 may be programmed such that it will only recognize data from a transmitter with a certain unique identifier. Memory 645 may be programmed via programming port 650.

Programming port 650 is provided to allow firmware and/or a unique identifier to be programmed. Any suitable interface may be used.

Transmitter 615 may be provided to transmit data to base device 150. Transmitter 615 may communicate via any wired or wireless, digital or analog interface or connection including a Wireless Application Protocol (WAP) link, a General Packet Radio Service (GPRS) link, a Bluetooth radio link, an IEEE 802.11-based radio frequency link, a RS-232 serial connection, an IEEE-1394 (Firewire) connection, a Fibre Channel connection, an infrared (IrDA) port, a Small Computer Systems Interface (SCSI) connection, or a Universal Serial Bus (USB) communication. Other non-protocol based communication methods may also be employed. Transmitter 615 may transmit data to base device 150 at a predetermined interval, such as once every minute. Other intervals may be used as required.

In one embodiment, the same data may be transmitted multiple times during the predetermined interval. For example, if the predetermined time interval is one minute, the same data may be transmitted three times during the predetermined interval. These transmissions may occur at random intervals during the predetermined interval. This provides redundancy to the transmission.

The operation frequency and power are set so that transmitter 615 can communicate with base device 150. Preferably, the operation frequency and power are in compliance with FCC and FDA requirements.

In one embodiment, prior to transmitting, transmitter 615 checks to ensure that no other transmitter within range are transmitting. This reduces the likelihood of data corruption.

Resistor Rshunt 655 and switch 660 are provided to set the range of the sensor. When switch 660 is closed, the resistance seen is 1 K ohm. This sets the range of the sensor at greater than 1 μA. If switch 660 is opened, the resistance seen is 1 M ohm. This sets the range of the sensor at less than 1 μA.

Figure 7:
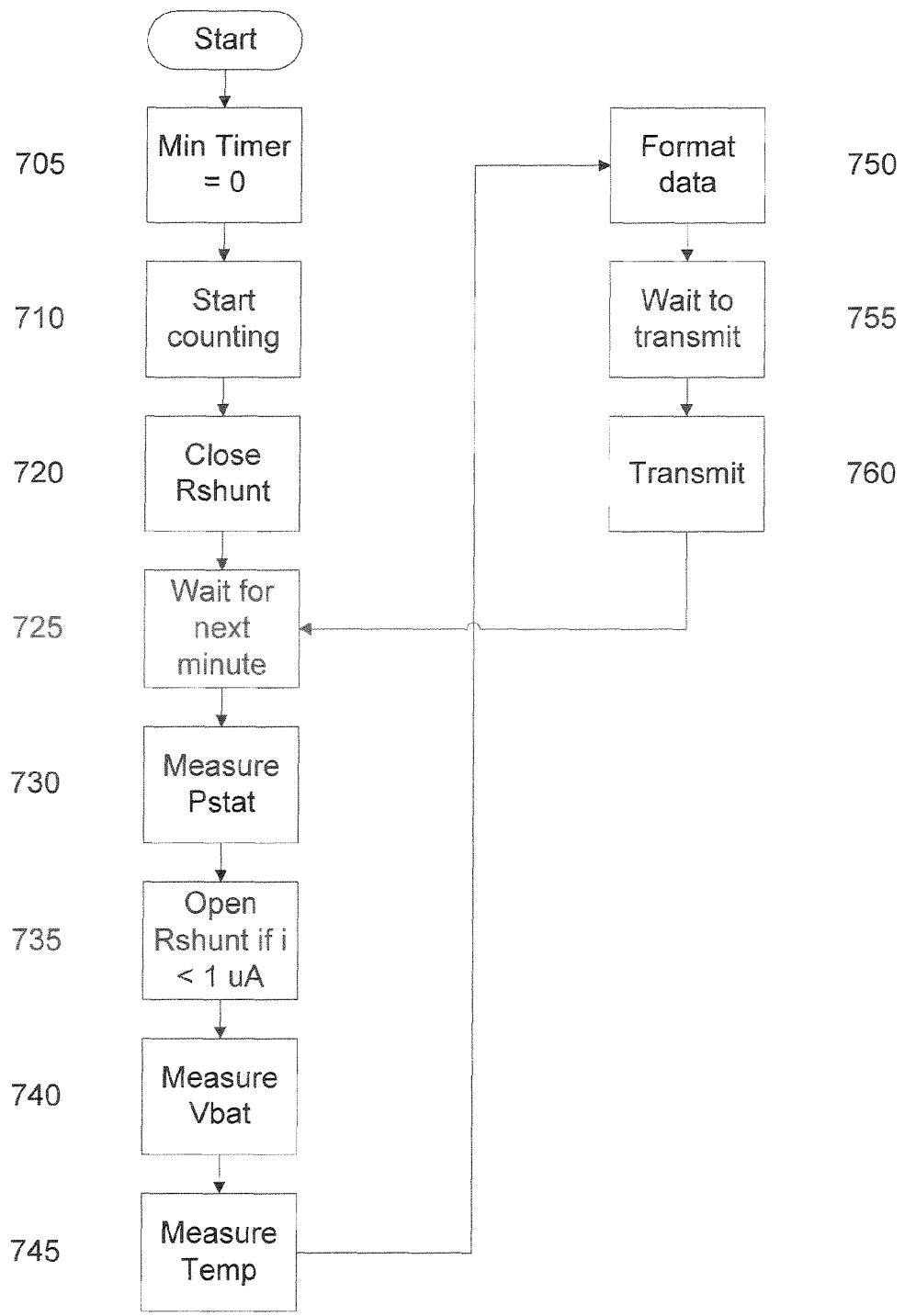
FIG. 7 is an illustration of a state machine executed by controller according to one embodiment of the present invention.

FIG. 7 is an illustration of a state machine executed by controller 640. At state 705, if the power is on, the state machine proceeds to state 710.

In state 710, the timer is reset (i.e., the timer is set to zero) and then started. In state 720, shunt resistor Rshunt is closed. Resistor Rshunt switches in or out a 1 k ohm resistor that is in parallel with the 1 M ohm sense resistor. When resistor Rshunt is open, the measurement resistance is 1 M ohm. Thus, a current of 1 μA is measured as a drop of 1 volt across the resistor. Essentially this provides a very sensitive gain of 1V/1 μA.

When resistor Rshunt is closed, the measurement resistance is 1K ohm in parallel with 1 M ohms, or 999 Ohms (approximately 1 K ohm). The 1 μA now represents a 1 mV drop across the resistor. This reduces the sensitivity to 1 mV/μA.

During sensor conditioning the sensor operates at higher currents therefore the 1 mV/μA gain is used. Once the sensor stabilizes at a lower current, the resistor Rshunt is opened and a gain of 1V/μA is used.

In state 725, the system waits for a predetermined passage of time, such as a minute. Once that predetermined time is met, in states 730, 740, and 745 measurements are made or captured. For example, in step 730, the current at potentiostat 725 is measured. If the current is less than 1 μAmp, in step 735, shunt resistor Rshunt is opened.

In state 740, the voltage at battery 620 is measured, and at state 745 the subject's temperature is measured.

Figure 8:
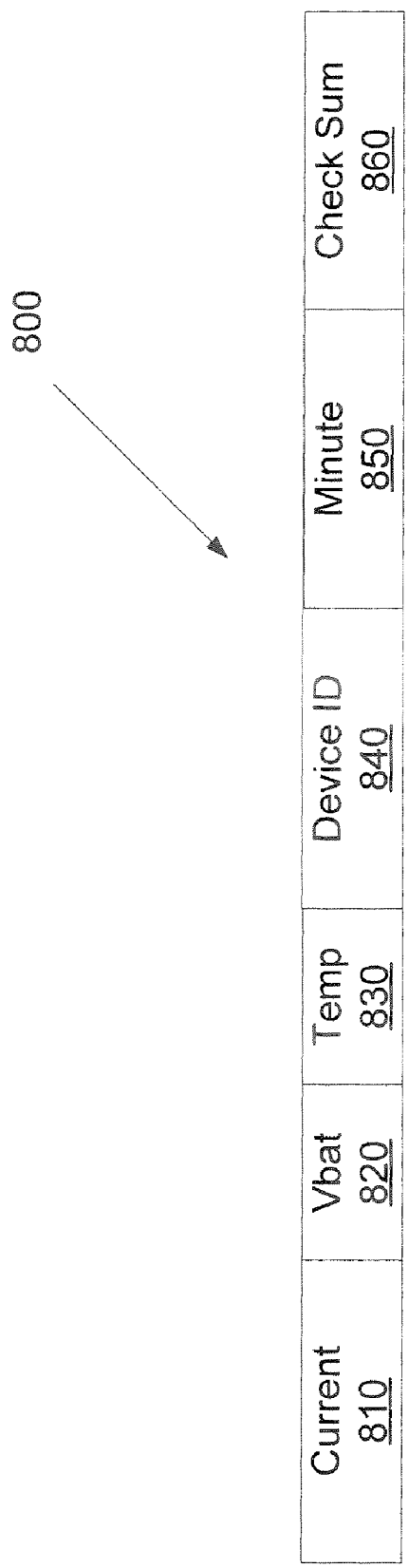
FIG. 8 is a data format in accordance with one embodiment of the present invention is provided.

In state 750, the collected data is formatted for transmission. Any suitable data format may be used. Referring to FIG. 8, a data format in accordance with one embodiment of the present invention is provided. Data format 800 includes current field 810, battery voltage field 820, subject temperature field 830, device identification number field 840, minute field 850, and checksum 860. Rshunt field (not shown) may be provided to indicate whether Rgain is shunted or not shunted. Additional or fewer fields may be included as necessary and/or desired.

In one embodiment, current field 810 may have a width of 16 bits, battery voltage field 820 may have a width of 7 bits, subject temperature field 830 may have a width of 8 bits, device identification number field 840 may have a width of 16 bits, minute field 850 may have a width of 16 bits, and checksum 860 may have a width of 16 bits.

Referring again to FIG. 7, in state 755, the state machine waits to transmit the formatted data. In one embodiment, the state machine waits to ensure that no other devices are transmitting at the same time.

In state 760, the formatted data is transmitted to base device 150. Following transmission, the state machine loops back to state 725.

Referring again to FIG. 1, base device 150 receives the signal transmitted from remote device 110. Base device 150 processes the received signal, resulting in a signal that is indicative of the predicted analyte concentration in the subject.

Figure 9:
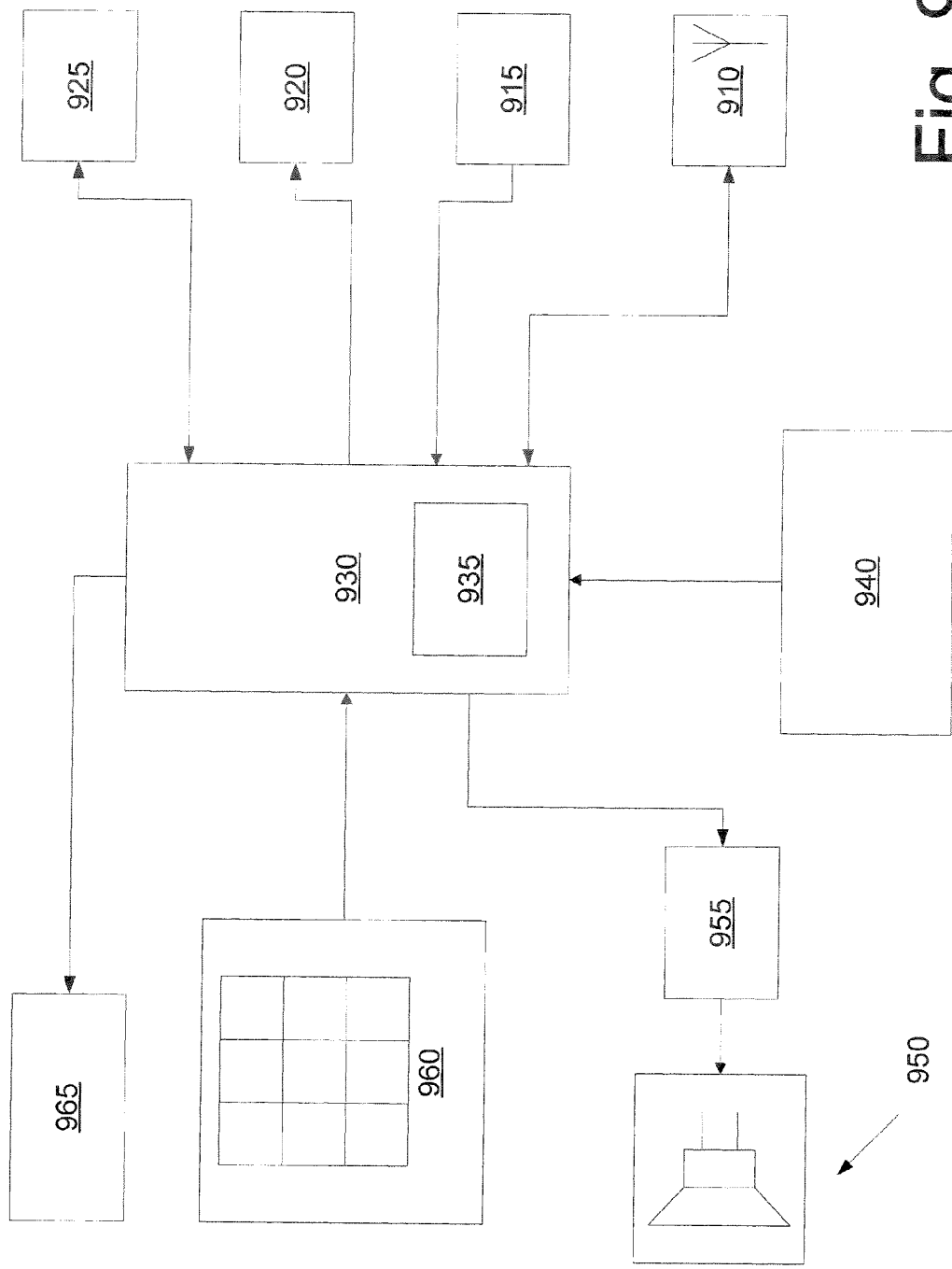
FIG. 9 is a schematic for a base device according to one embodiment of the invention.

Referring to FIG. 9, schematics for base device 150 according to one embodiment of the invention are provided. Base device 150 includes receiver 910 that receives the signal transmitted by remote device 110. In one embodiment as base device 150 receives data from remote device 110, the data is error checked and written to non-volatile memory 935. This will be described in greater detail, below.

In one embodiment, base device 150 monitors the operation of remote device 110. In one embodiment, when base device 150 detects that remote device 110 has been transmitting for a predetermined time, indicating that remote device is attached to a subject, base device 150 prompts the operator to enter calibration data from the blood draw. The calibration data may be a time-stamped measurement of the subject's glucose level taken from a venous blood sample or finger stick meter reading. Preferably, this may take place after one hour of operation. Therefore the blood draw time and date occur between Sensor On+1 hour and the Current Sensor Time.

Programming port 915 is provided in the same manner as programming port 550.

Interface 920 is provided to allow access to the data stored and/or received by base device 150. In one embodiment this may be a RS-232 serial connection. Other communications protocols, such as a Wireless Application Protocol (WAP) link, a General Packet Radio Service (GPRS) link, a Bluetooth radio link, an IEEE 802.11-based radio frequency link, an EEE-1394 (Firewire) connection, a Fibre Channel connection, an infrared (IrDA) port, a Small Computer Systems Interface (SCSI) connection, or a Universal Serial Bus (USB) connection may also be used.

Interface 920 may also transmit data to the hospital's patient database and to a patent terminal, central nurse's station, etc.

In one embodiment, seven days worth of data will be stored in a buffer and downloaded via interface 920.

Clock 925 is provided. In one embodiment, clock 925 is used to time-stamp data that is received from remote device 110.

Base device 150 is provided with processor 930. Processor 930 may be either a 16 or 18-series microcontroller. For example, the MicroChip PIC-18 family of processors may be used. In one embodiment, processor 930 preferably includes an internal analog to digital converter (not shown) and program memory (not shown). Processor 930 also preferably includes memory 935, such as a nonvolatile memory. Memory 935 can be located internal to processor 930, or it can be located external to processor 930. In one embodiment, memory 935 should be of adequate size to hold a minimum of 24 hours worth of data.

Processor 930 executes software, firmware, and/or microcode. This will be discussed in greater detail, below.

Memory 935 may store a unique identification code in the same manner as memory 645.

Base device 150 includes a power supply, such as battery pack 940. In one embodiment, battery pack 940 supplies base device 150 with power for 1 week without replacement. In one embodiment, battery pack 940 may be a rechargeable battery pack.

During operation, battery voltage may be monitored. This may require an analog to digital converter (not shown). If the voltage of battery pack 940 falls below a predetermined voltage, the operator is alerted. This may include a visual indication, or an audible indication. Preferably, powering-down base device 150, or replacing battery pack 940 does not result in any data being lost.

Alarm 950 and mute switch 955 are provided. In one embodiment, alarm 950 is a piezoelectric alarm that is used to alert the operator of certain events, alarm states and error conditions. These, as well as other types of alarms and notifications will be discussed in greater detail below.

In one embodiment, mute switch 955 is provided to mute or silence alarm 950.

Base device 150 may include an input device, such as keypad 960. Keypad 960 may include several input switches, such as nine poly dome-type switches, that are used to input data and control remote device 110 and/or base device 150 in another embodiment a touch-screen may be used.

Base device 150 also includes display 965. In one embodiment, display 965 is a liquid crystal display. The operating characteristics of display 965 may be configured (e, contrast, viewing angle, backlight, etc.) as necessary.

Display 965 may graphically present information to a user in real time. For example, in one embodiment of the invention a subject's glucose level may be graphically displayed for a certain period of time. Notable events, such as actual blood measurements, injections of insulin, etc. may be graphically displayed on the timeline so that the impact of such on the subject's glucose level may be viewed.

Other parameters, such as the subject's glucose rate of change, temperature, and temperature rate of change, may also be graphically displayed. In addition to display 965, base device 150 may also include LEDs (not shown) as necessary to provide status information (e.g., power on/off, battery status, etc.) to the user.

Figure 10:
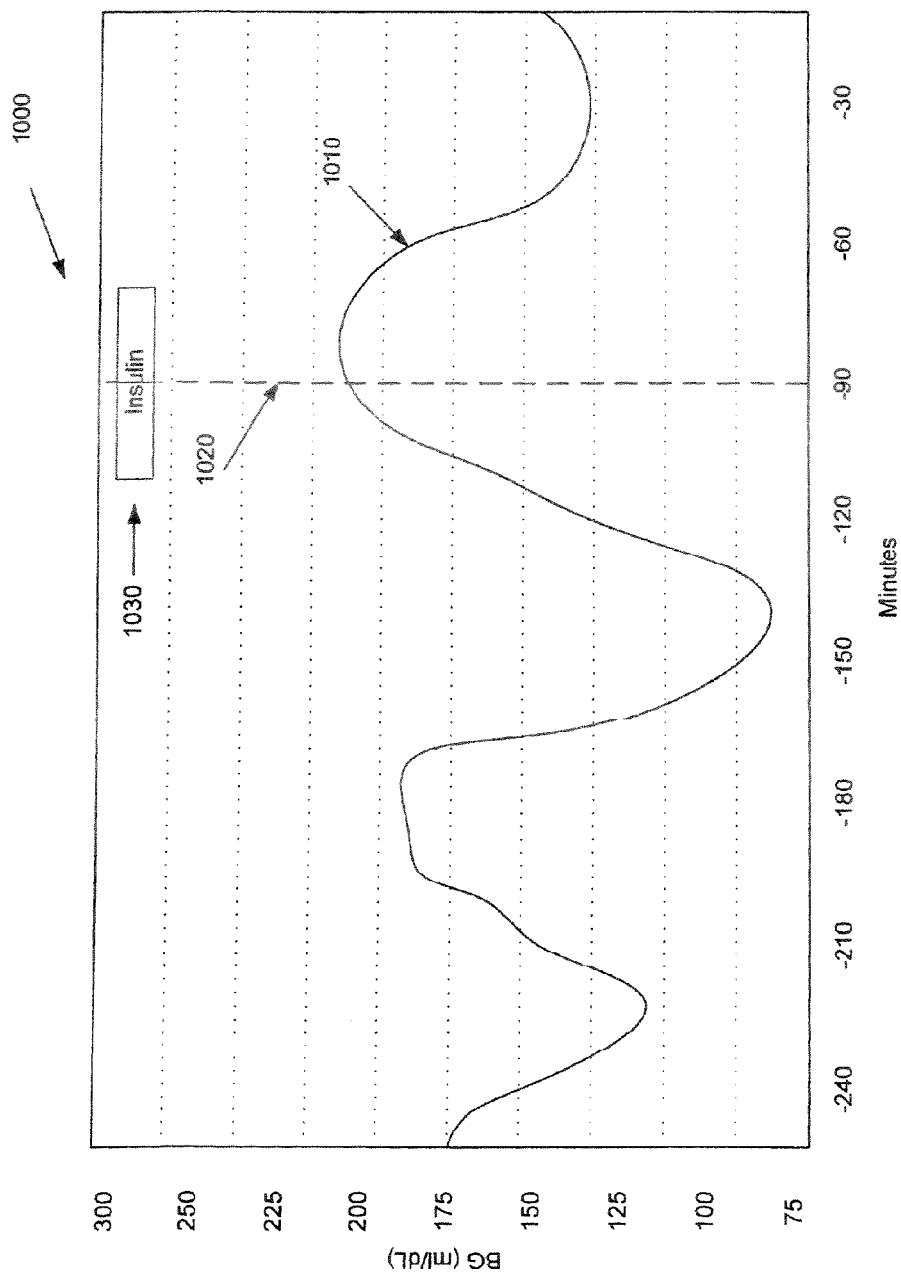
FIG. 10 is an example of a display according to one embodiment of the present invention.

Referring to FIG. 10, an example of a display according to one embodiment of the present invention is provided. Display 1000 includes graphical representation 1010 of blood glucose versus time. In one embodiment, graphical plot 1010 for the past four hours is displayed; other time periods may be displayed as desired. In another embodiment, the scales may be selected by a user.

Marker 1020 may be provided to indicate when insulin was administered to the subject. In one embodiment, marker 1020 may comprise a vertical line, such as that shown in FIG. 10, Label 1030 may also be provided to indicate what marker 1020 is marking. In another embodiment, marker 1020 may be selected by a user such that it most effectively indicates the time at which the insulin was administered Marker 1020 may also provide additional information, such as the doseage of the insulin, the person who administered the insulin, and the time of that the administration occurred. This may be continuously provided in display 1000, or it may be provided in a drop-down box (not shown) that is selected by a user.

Figure 11:
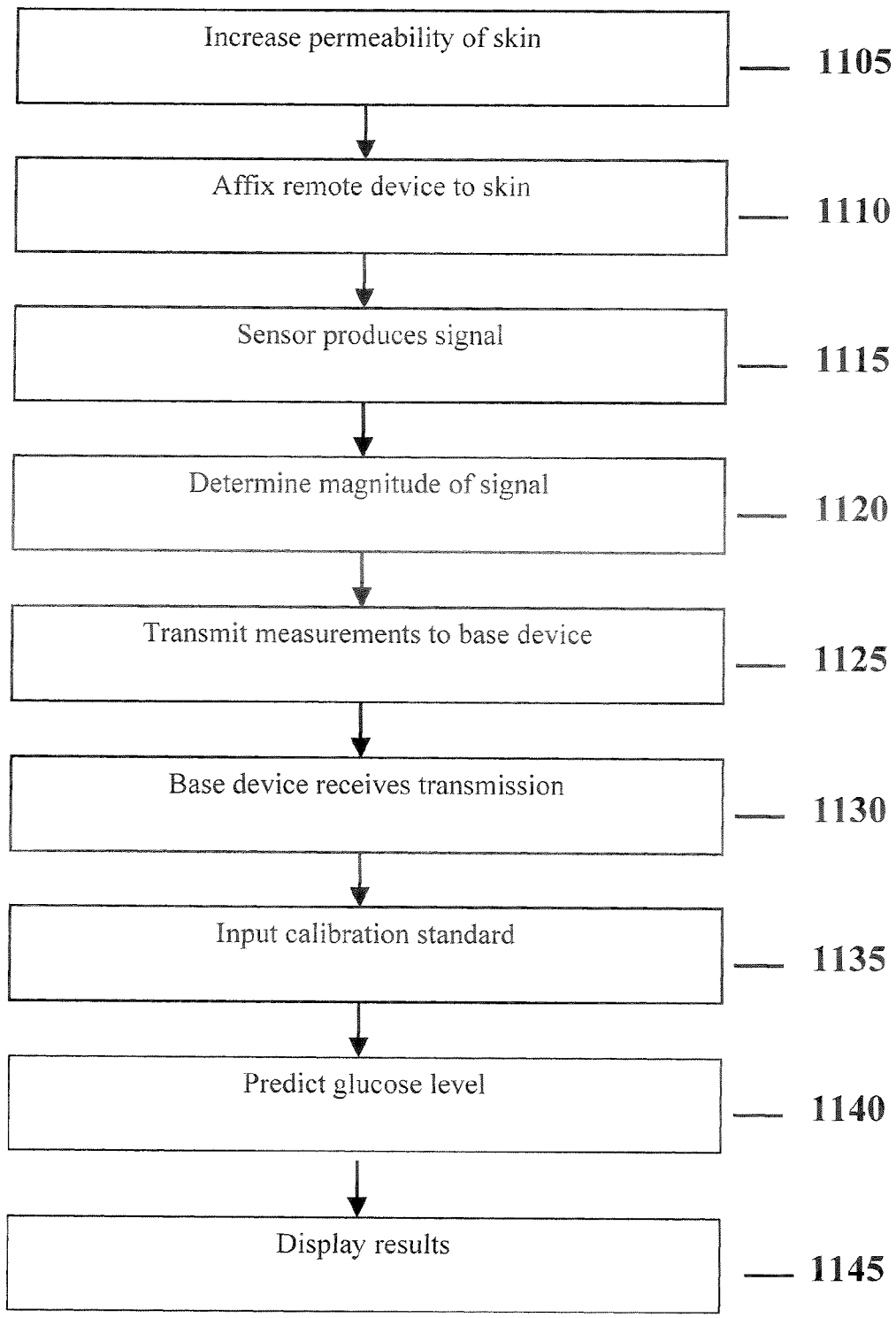
FIG. 11 is an illustration of a method for continuous, non-invasive monitoring of a subject's glucose level according to one embodiment of the present invention.

FIG. 11 illustrates a method 1100 for continuous, noninvasive monitoring of a subject's glucose level, preferably in an intensive care unit, according to one embodiment of the invention. In some embodiments, method 1100 may be performed by system 100 of FIG. 1.

In step 1105, the permeability of an area of a subject's skin is increased. This may be accomplished by any suitable mechanism, including the application of ultrasound, mechanical disruption, laser skin ablation, electroporation, RF ablation, microneedles, chemical peel, etc. In one embodiment, the SonoPrep® Skin Permeation Device, available from Sontra Medical Corp., Franklin, Mass., may be used to increase the permeability of the area of skin. Other devices, such as the QuickPrep™ automated patient prep system available from Quinton, Inc., 303 Monte Villa Parkway, Bothell, Wash. 98021-8906, may also be used.

In step 1110, the remote device is positioned and affixed to the area of skin. Preferably, remote device is affixed to the area of skin by a medical grade adhesive. Remote device should be securely affixed so that it is not unintentionally removed from the area of skin, but not preferably does not cause significant skin damage when removed.

A medium may be provided between the surface of the skin and the sensor in order to keep the two in aqueous contact. In one embodiment, a hydrogel disc may be positioned between the skin and the sensor. Referring to FIG. 4, the hydrogel disc is preferably inserted in the interior portion of adhesive ring 405.

Referring again to FIG. 11, in step 1115, once the remote device is affixed, the sensor begins to produce a signal, such as an amperometric current, that is representative of a subject's glucose level. In step 1120, the magnitude of the signal is measured, and may associated with the current time (i time-stamped). Additionally, other modules, such as the temperature module and the battery module, may measure the subject's skin temperature and the voltage level of the a battery, respectively. These measurements may also be time-stamped.

In step 1125, the time-stamped measurements may be transmitted from the remote device to the base device. As discussed above, this transmission may be made by any suitable wired or wireless protocol. Prior to transmission, a unique identification number and checksum value may be added to this data in order to produce a secure and accurate transmission.

In step 1130, the base device receives the transmitted data and stores it in memory. In one embodiment, the base device may verify the integrity of this transmitted data. This may be accomplished through the use of a checksum value. In addition, the identification number may be compared to one that is stored in the base device's memory.

At step 1135, the user may input at least a glucose calibration standard for the subject. This calibration standard may be a time-stamped measurement of the subject's glucose level taken from a venous blood sample or finger stick meter reading. The user may input this calibration standard through the use of a keypad or other input device attached to the base device.

At step 1140, the base device may combine the time-stamped data representing the current produced by the remote device and the inputted calibration standard to predict the value of the subject's glucose level. The base device may calculate the predicted glucose value, current, and percent change in skin temperature by using the following equations:

Predicted Glucose$_t$=I$_t$×(Measured Glucose$_{t=cal}$/I$_{t=cal}$);

I$_t$=sensor current−baseline; and

Displayed Temp$_t$=(Temp$_t$/Temp$_{t=cal}$)×100 where baseline is a preprogrammed value in nA.

Predicted Glucose Rate of change=Predicted Glucose$_T$−Predicted Glucose$_{T-1}$ Predicted glucose displayed may also be adjusted to compensate for temperature changes and temporal changes. This is discussed in greater detail in U.S. patent application Ser. No. 10/974,963, entitled "System and Method for Analyte Sampling and Analysis," the disclosure of which is incorporated by reference in its entirety.

In some embodiments of the method, these calculations may be performed by the prediction module using a microcontroller.

At step 1145, the base device displays this data, including data representing the current in the remote device; the subject's predicted glucose value; the predicted rate of change of the subject's glucose value and a future estimated glucose value (T+10 minutes, for example) based on the rate of change; the voltage of the batteries in either remote device, base device, or both; the percent change of the subject's skin temperature; and the status of the piezo alarm. The number of minutes that have elapsed since the remote device was first attached to the subject may also be displayed.

In one embodiment, the results may be displayed graphically, as discussed above with reference to FIG. 10.

As discussed above, the method and device of the present invention included an alarm function that provides an audible and/or visual notification when predetermined conditions are met. In one embodiment, the following alarms may be provided: (1) hypoglycemic; (2) hypoglycemic anticipated; (3) hyperglycemic; (4) hyperglycemic anticipated; (5) low remote device battery; (6) low base device battery; (7) communication link lost; (8) communication link disturbed; (9) bad sensor data; (10) 1 hour left; and (11) 24 hours exceeded. Other alarms may be provided as necessary and desired.

These messages may also be transmitted to and displayed on a patient terminal via a central database, and/or displayed at a central nurse's station.

In general, a single measurement that meets a predetermined condition is insufficient to trigger an alarm. Rather, two (or more) consecutive alarm conditions are required to trigger the alarm. The number of consecutive alarm conditions may be increased or decreased as necessary and/or desired.

Each of these alarms will be discussed in greater detail below. Although a variety of conditions precedent for each alarm may be used, a set of preferred conditions will be discussed.

The hypoglycemic alarm may be triggered when two consecutive glucose predictions are below a preset limit. In one embodiment, the preset limit may be 60 mg/dl. In addition, the preset limit may vary from subject to subject.

The hypoglycemic anticipated alarm may be triggered when five minute averaged rate of change predicts that two consecutive glucose readings will be below the hypoglycemic preset limit within ten minutes.

The hyperglycemic alarm may be triggered when two consecutive glucose predictions are above a preset limit. In one embodiment, the preset limit may be 200 mg/dl. In one embodiment, the preset limit may be 160 mg/dl. In addition, as with the preset limit for the hypoglycemic alarm, the preset limit may vary from subject to subject.

The hyperglycemic anticipated alarm may be triggered when five minute averaged rate of change predicts that two consecutive glucose readings will be above the hyperglycemic preset limit within ten minutes.

The low remote device battery and low base device battery alarms may be triggered when the measured voltage on either battery falls below a predetermined voltage. In one embodiment, the predetermined voltage may be set in order to provide at least a certain amount of time before the battery fails. For example, when the battery voltage for the remote device falls below 2.8 VDC for two consecutive transmissions, or when the battery voltage for the remote device falls below 6.0 VDC, the respective alarms are triggered.

Power-saving techniques, such as a reduction in power to the display, may be employed to conserve power once the alarm condition is met.

The communication link lost alarm may be triggered when two consecutive measurements are missed.

The communication link disturbed alarm may be triggered when two consecutive data streams with valid identification code have invalid check sum values.

The bad remote device data alarm may be triggered when two consecutive data streams have sensor currents below a predetermined value, such as 10 nA (any time) or above a predetermined value, such as 1 uA, after a certain period of operation, such as 35 minutes.

The 1 hour left alarm may be triggered when two consecutive data streams report times greater than 1380 minutes (i.e., 23 hours).

The 24 hours exceeded alarm may be triggered when two consecutive data streams report times greater than 1440 minutes (i.e., 24 hours)

The alarms may be displayed until the mute switch is pressed. In the case of multiple alarms, the base device may queue the alarms in a first in first out sequence. Each time the mute switch is pressed, the current alarm will be cleared and the next alarm in the queue will be displayed. In one embodiment, certain alarms, such as hypoglycemic and hyperglycemic will have priority over all other alarms and be displayed regardless of their position in the queue.

Figure 12:
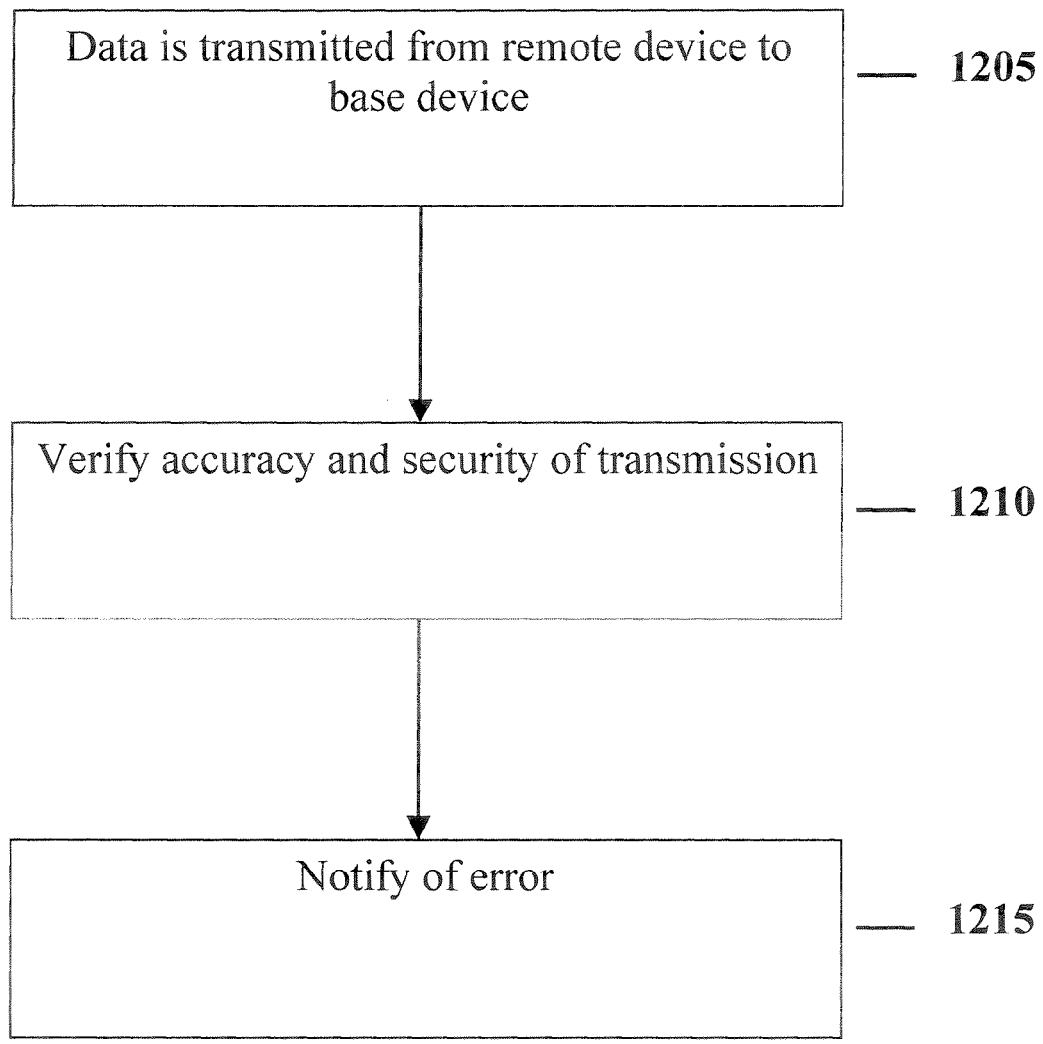
FIG. 12 illustrates a method for identifying errors in the transmission of data according to one embodiment of the present invention.

FIG. 12 illustrates a method for identifying errors in the transmission of data. In step 1205, data may be transmitted wirelessly between the remote device and the base device of the system. As discussed above, in some embodiments, this data may contain a measurement of the current produced at remote device, a measurement of the subject's skin temperature, and a measurement of the transmitter unit's battery. This data may also have been formatted to include a timestamp value, checksum value, and a ID number.

In step 1210, the security and accuracy of this transmitted data may be verified. In one embodiment of the method, an error module may use a microprocessor to compare the timestamp of the most recent data transmission to that of previous transmissions, to compare the data identification f the most recent data transmission to that which is stored in the base device's memory, to verify the transmitted data's checksum value, and to analyze the value of the current produced in the remote device.

In step 1215, the system may notify the user if the data is found to be insecure or inaccurate. In one embodiment of the method, the error module may sound an alarm if (1) a comparison of the data timestamps shows that two consecutive transmissions have been missed (2) two consecutive data transmissions have incorrect checksum values (3) a predetermined number of measurements for the current in remote device are below or above certain preset values. In one embodiment, it two measurements are below or above the preset values, the alarm is activated.

in one embodiment, system 100 may interface with a mechanism for providing insulin. Thus, with this addition, not only is the hypoglycemic or hypoglycemic conditions detected and/or predicted, but the conditions are appropriately treated automatically. In one embodiment, the initiation of treatment requires human authorization, the insulin cannot be administered without a human authorizing the administration. In other embodiments, human authorization is only required for the administration of insulin in extreme conditions.

The present invention contemplates a system that continuously monitors the amount of insulin treatment and the effect of that insulin treatment on the subject's glucose level. Because the effect of insulin on a glucose level will vary from subject to subject, and even within the same subject, the system may attempt to determine an optimum insulin treatment based on past performance. However, until several insulin treatments are observed, it may be difficult for the contemplated system to accurately determine the amount of an insulin treatment required. Therefore, until a sufficient number of observations have been completed, the system may require all insulin to be administered by a human.

The various embodiments of the systems and methods described and claimed herein provide numerous advantages. For example, the systems and methods permit continuous, noninvasive detection of a subject's glucose levels. Thus, a user can monitor the a subject's post operative glucose levels more frequently, effectively, and comfortably. Such improved systems and methods for monitoring post operative glucose levels may help to reduce a subject's risk of infection and reduce hospitalization.

Other embodiments, uses, and advantages of the present invention will be apparent to those skilled in the art from consideration of the specification and practice of the invention disclosed herein. The specification and examples should be considered exemplary only.

What is claimed is:

1. A method for real time remote monitoring and display of a level of at least one analyte in a body fluid of a subject, comprising:

contacting a remote device to an area of biological membrane having a permeability level, the remote device comprising a sensor and a transmitter;

extracting the analyte through and out of the area of biological membrane and into the sensor;

generating an electrical signal representative of a level of the analyte;

transmitting the electrical signal to a base device;

processing the electrical signal to determine the level of the analyte and the rate of change of the level of analyte, wherein the one or more future analyte level(s) are calculated based on the determined level of analyte and an average of the determined rate of change of the level of analyte;

displaying the level of the at least one analyte in real time; and triggering an alarm if (1) one or more determinations of the level of analyte is/are below a hypoglycemic preset limit or above a hyperglycemic preset limit and (2) the determined rate of change of the level of analyte predicts that one or more future analyte level(s) will be below the hypoglycemic preset limit or above the hyperglycemic preset limit within a period of time.

2. The method of claim 1, wherein the at least one analyte is glucose.

3. The method of claim 1, further comprising the step of:
increasing the permeability level of the area of biological membrane.

4. The method of claim 1, wherein the step of contacting a remote device to an area of biological membrane having a permeability level comprises:

affixing the remote device to the area of biological membrane with an adhesive.

5. The method of claim 1, wherein the step of transmitting the signal to a base device comprises:

converting the electrical signal representative of the level of the at least one analyte to a digital signal; and transmitting the digitized signal, an identification number of the remote device, and a time stamp to the base device.

6. The method of claim 1, wherein the step of transmitting the signal to a monitoring device is performed periodically.

7. The method of claim 1, wherein step of the transmitting the electrical signal to a base device comprises:

transmitting the signal to the base device by at least one of a wireless application protocol link, a general packet radio service link, a Bluetooth radio link, an IEEE 802.11-based radio frequency link, a RS-232 serial connection, an IEEE-1394 (Firewire) connection, a fibre channel connection, an infrared (IrDA) port, a small Computer Systems Interface (SCSI) connection, and a Universal Serial Bus (USB) connection.

8. The method of claim 1, further comprising the step of:
periodically determining an amount of a drug to be injected in response to the analyte level; and
automatically providing the determined amount of the drug to the subject.

9. The method of claim 8, wherein the drug is insulin.

10. The method of claim 1, wherein the analyte level is displayed graphically.

11. The method of claim 10, wherein the analyte level is displayed in relative to time.

12. The method of claim 1, wherein the alarm is triggered if (1) two consecutive determinations of the level of analyte are below the hypoglycemic preset limit or above the hyperglycemic preset limit and (2) the determined rate of change of the level of analyte predicts that two consecutive future analyte levels will be below the hypoglycemic preset limit or above the hyperglycemic preset limit within a period of time.

13. The method of claim 12, wherein the average is a five-minute average and the period of time is ten minutes.

* * * * *